US010443030B2

(12) United States Patent
Hiatt et al.

(10) Patent No.: US 10,443,030 B2
(45) Date of Patent: *Oct. 15, 2019

(54) SOLID WASTE DIGESTION SYSTEM

(71) Applicant: Eco Sphere Sciences, Inc., Carson City, NV (US)

(72) Inventors: William Nicholas Hiatt, Signal Hill, CA (US); Mohammed Memon, Huntington Beach, CA (US); Jacob J. L. Dickinson, Long Beach, CA (US); James DeWitt Stein, Redondo Beach, CA (US); Gary Ailes, Carson City, NV (US)

(73) Assignee: Eco Sphere Sciences, Inc., Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/796,350

(22) Filed: Oct. 27, 2017

(65) Prior Publication Data

US 2018/0051245 A1    Feb. 22, 2018

Related U.S. Application Data

(63) Continuation of application No. 14/270,140, filed on May 5, 2014, now Pat. No. 9,822,332, which is a (Continued)

(51) Int. Cl.
*C02F 3/30* (2006.01)
*F23G 5/02* (2006.01)
(Continued)

(52) U.S. Cl.
CPC ............. *C12M 41/46* (2013.01); *C02F 3/301* (2013.01); *C12M 21/16* (2013.01); *C12M 27/06* (2013.01); *C12M 41/34* (2013.01); *C12P 5/023* (2013.01); *F23G 5/02* (2013.01); *F23G 2201/701* (2013.01); *F23G 2201/80* (2013.01); *F23G 2900/50208* (2013.01);
(Continued)

(58) Field of Classification Search
CPC ...... C12M 41/46; C12M 21/16; C12M 41/34; C12M 27/06; C02F 3/301; C12P 5/023; F23G 5/02; F23G 2900/7009; F23G 2900/50208; F23G 2201/80; F23G 2201/701; Y02W 10/37; Y02E 50/343
USPC ....... 210/602, 605, 612, 613, 614, 629, 630, 210/173, 252, 259
See application file for complete search history.

(56) References Cited

U.S. PATENT DOCUMENTS 3,142,557 A * 7/1964 MacDuffie .............. C05F 17/00
71/9
3,768,200 A * 10/1973 Klock .................... A01G 33/00
47/1.4
(Continued)

*Primary Examiner* — Fred Prince
(74) *Attorney, Agent, or Firm* — Jeffrey G. Sheldon; Cislo & Thomas LLP

(57) ABSTRACT

A system for digesting biodigestible feed that preferably includes the steps of comminuting the feed, introducing feed, an oxygen-containing gas, an accelerant, and bacteria into a digestion zone, the bacteria being suitable for digesting the feed under aerobic, anaerobic, and anoxic conditions. The contents of the digestion zone can be changed from aerobic operation to either anoxic or anaerobic operation, or vice versa, without changing the bacteria in the digestion zone.

13 Claims, 5 Drawing Sheets

Related U.S. Application Data continuation of application No. 13/068,849, filed on Jul. 13, 2010, now Pat. No. 8,715,501.

(51) Int. Cl.
  *C12P 5/02* (2006.01)
  *C12M 1/34* (2006.01)
  *C12M 1/16* (2006.01)
  *C12M 1/06* (2006.01)

(52) U.S. Cl.
  CPC ..... *F23G 2900/7009* (2013.01); *Y02E 50/343* (2013.01); *Y02W 10/37* (2015.05)

(56) References Cited

U.S. PATENT DOCUMENTS

| | | | | |
|---|---|---|---|---|
| 4,053,394 A * | 10/1977 | Fisk | ............ | C02F 3/30 210/605 |
| 4,710,301 A * | 12/1987 | Geuens | ............ | C02F 9/00 210/605 |
| 5,013,442 A * | 5/1991 | Davis | ............ | C02F 3/006 210/143 |
| 5,545,326 A * | 8/1996 | Petering | ............ | C02F 3/308 210/195.1 |
| 5,582,734 A * | 12/1996 | Coleman | ............ | C02F 3/006 210/614 |
| 5,650,070 A * | 7/1997 | Pollock | ............ | C02F 3/223 210/199 |
| 5,702,499 A * | 12/1997 | Timmenga | ............ | C05F 17/0018 71/6 |
| 5,744,041 A * | 4/1998 | Grove | ............ | C02F 3/30 210/602 |
| 6,025,152 A * | 2/2000 | Hiatt | ............ | A01K 63/04 435/262 |
| 6,203,700 B1 * | 3/2001 | Rose | ............ | C02F 1/62 210/602 |
| 6,296,766 B1 * | 10/2001 | Breckenridge | ............ | C02F 3/006 210/603 |
| 6,299,774 B1 * | 10/2001 | Ainsworth | ............ | C02F 3/28 210/178 |
| 6,514,411 B2 * | 2/2003 | Pressley | ............ | B01F 3/0876 210/194 |
| 6,562,585 B1 * | 5/2003 | Hiatt | ............ | C02F 3/308 435/42 |
| 6,569,332 B2 * | 5/2003 | Ainsworth | ............ | C02F 3/28 210/178 |
| 6,616,843 B1 * | 9/2003 | Behmann | ............ | C02F 3/006 210/143 |
| 6,660,164 B1 * | 12/2003 | Stover | ............ | C02F 3/006 210/143 |
| 6,663,777 B2 * | 12/2003 | Schimel | ............ | C02F 3/006 210/138 |
| 6,733,662 B2 * | 5/2004 | Pollock | ............ | C02F 3/1268 210/143 |
| 6,869,534 B2 * | 3/2005 | McDowell | ............ | C02F 3/006 210/195.1 |
| 6,942,801 B2 * | 9/2005 | Nishimura | ............ | C02F 11/02 210/150 |
| 6,955,757 B1 * | 10/2005 | Maltin | ............ | C02F 3/121 210/150 |
| 7,001,519 B2 * | 2/2006 | Linden | ............ | A01K 63/04 119/227 |
| 7,024,796 B2 * | 4/2006 | Carin | ............ | C05F 3/00 34/363 |
| 7,481,940 B2 * | 1/2009 | Clifford, III | ............ | C02F 11/04 210/739 |
| 7,553,410 B1 * | 6/2009 | Chennault | ............ | C02F 3/12 210/150 |
| 7,556,737 B2 * | 7/2009 | Zhang | ............ | C02F 3/286 210/202 |
| 2002/0030003 A1 * | 3/2002 | O'Leary | ............ | C02F 3/006 210/151 |
| 2005/0098496 A1 * | 5/2005 | Hamann | ............ | B63B 29/16 210/605 |
| 2005/0269263 A1 * | 12/2005 | Rittmann | ............ | C02F 3/102 210/630 |
| 2006/0289356 A1 * | 12/2006 | Burnett | ............ | C02F 11/04 210/603 |
| 2007/0102353 A1 * | 5/2007 | Murthy | ............ | C02F 11/02 210/605 |
| 2008/0314828 A1 * | 12/2008 | Campbell | ............ | B09B 3/00 210/609 |
| 2010/0155313 A1 * | 6/2010 | Wilson | ............ | B09B 3/00 210/98 |

* cited by examiner

SOLID WASTE DIGESTION SYSTEM

CROSS-REFERENCE TO RELATED APPLICATIONS

The present application is a continuation of U.S. patent application Ser. No. 14/270,140, filed May 5, 2014, entitled, "Solid Waste Digestion System," which is a continuation of U.S. patent application Ser. No. 13/068,849, filed Jul. 13, 2010, entitled, "Solid Waste Digestion System," now U.S. Pat. No. 8,715,501, the contents of which are incorporated herein by reference.

BACKGROUND

A variety of processes are known that may be suitable for processing solid waste. See for example U.S. Pat. No. 3,142,557, M. MacDuffie; U.S. Pat. No. 4,053,394, Fisk; U.S. Pat. No. 5,702,499, Timmenga; U.S. Pat. No. 6,296,766, Breckenridge; U.S. Pat. No. 6,569,332, Ainsworth; U.S. Pat. No. 6,733,662, Pollock; U.S. Pat. No. 6,869,534, McDowell; U.S. Pat. No. 6,942,801, Nishimura; U.S. Pat. No. 6,942,801, Carin; U.S. Pat. No. 7,481,940, Clifford; U.S. Pat. No. 7,553,410, Chennault; U.S. Pat. No. 7,556,737, Zhang; U.S. Patent Publication No. 2006/0289356, Burnett; and U.S. Patent Publication No. 2008/0314828, Campbell.

However applicants believe there is no known process that is suitable for both anaerobic, anoxic and aerobic processing of solid and liquid waste, where conditions of the processing can be changed "on the fly". It is desirable to quickly change from anaerobic to aerobic or from aerobic to anaerobic to control the output from the process depending on feed stock and desired output.

The present invention is directed to a system that satisfies this need.

DRAWINGS

These and other features, aspects, and advantages of the present invention will become better understood with reference to the following description and accompanying drawings where:

Figure 3:
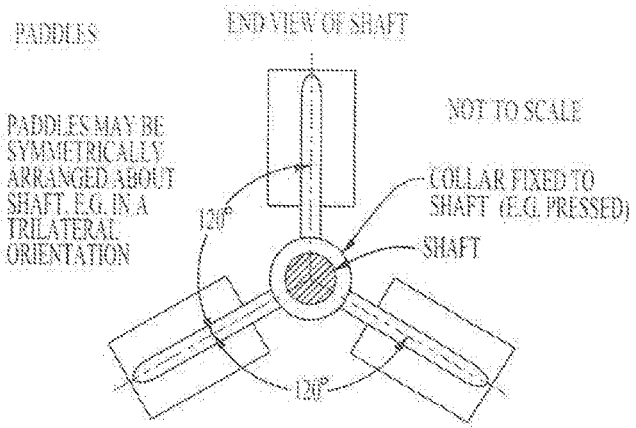
Figure 4:
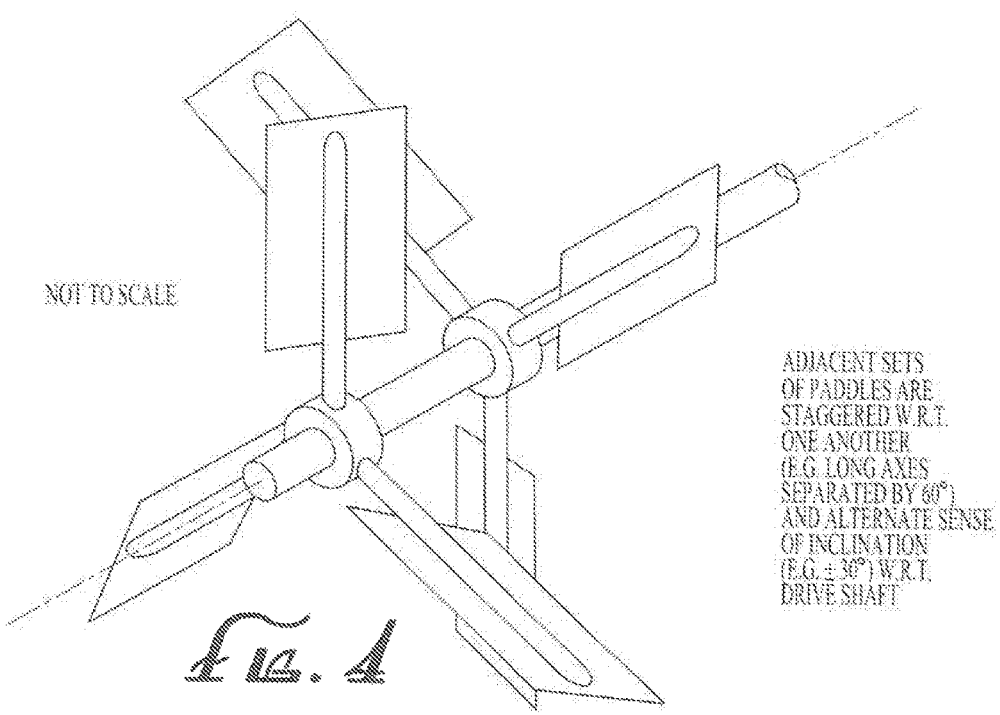
Figure 5:
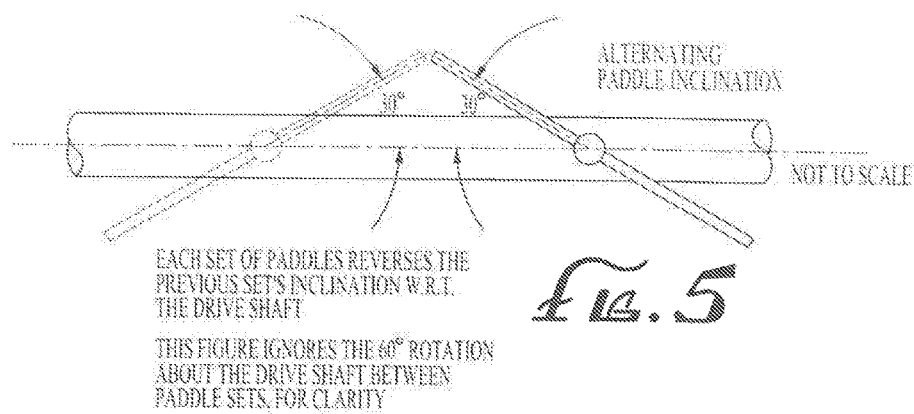
Figure 6:
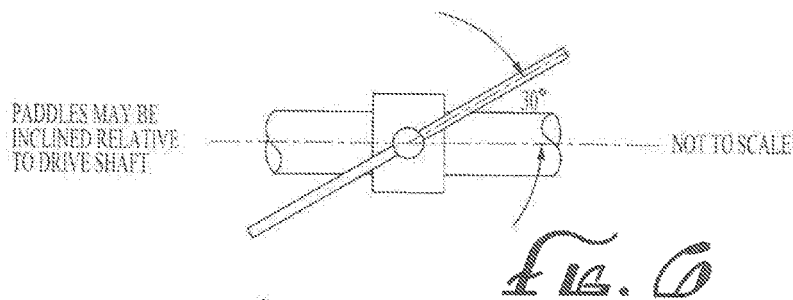
Figure 7:
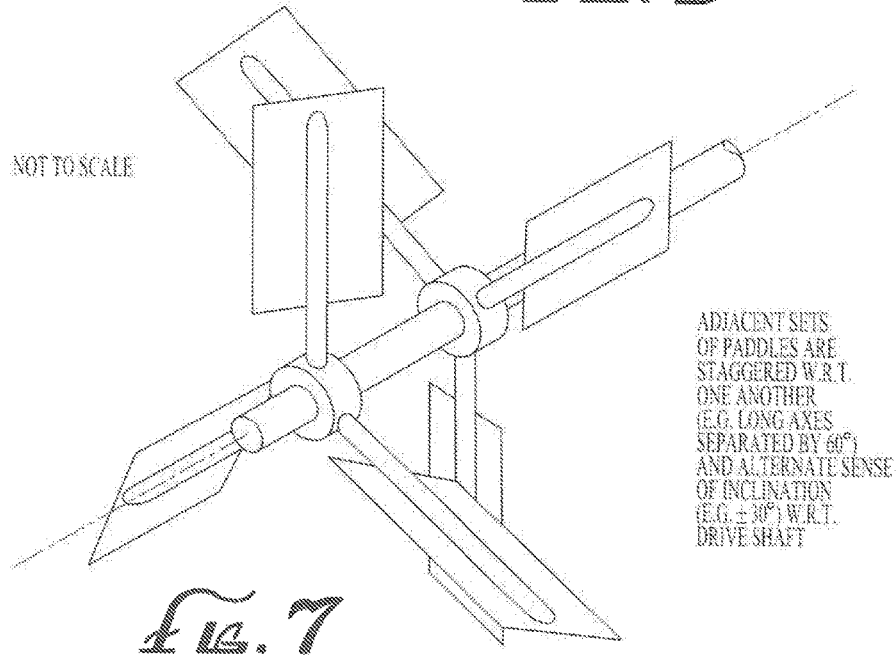
Figure 8:
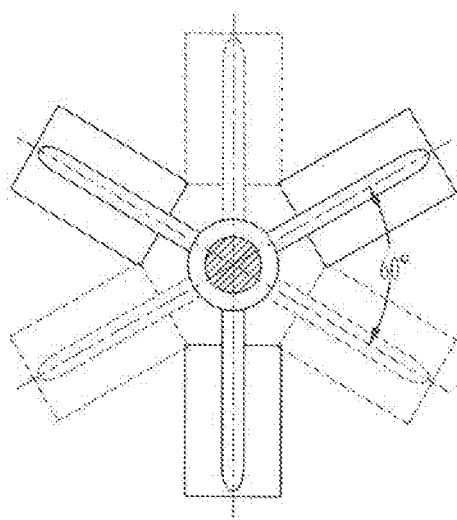

FIGS. 3 and 4 schematically show a preferred configuration of paddles for use in a digester where they are trilaterally symmetrical groups of paddles, wherein the paddles are not parallel to a drive shaft used for driving the paddles;

FIGS. 5 and 6 schematically show a paddle configuration where alternating groups of paddles are staggered with respect to one another, wherein proceeding along the drive shaft, each paddle is rotated 60° with respect to the next or proceeding paddle; and FIGS. 7 and 8 schematically shows the direction of paddle inclination with respect to the drive shaft can be reversed in alternating sets of paddles.

DESCRIPTION

Figure 1:
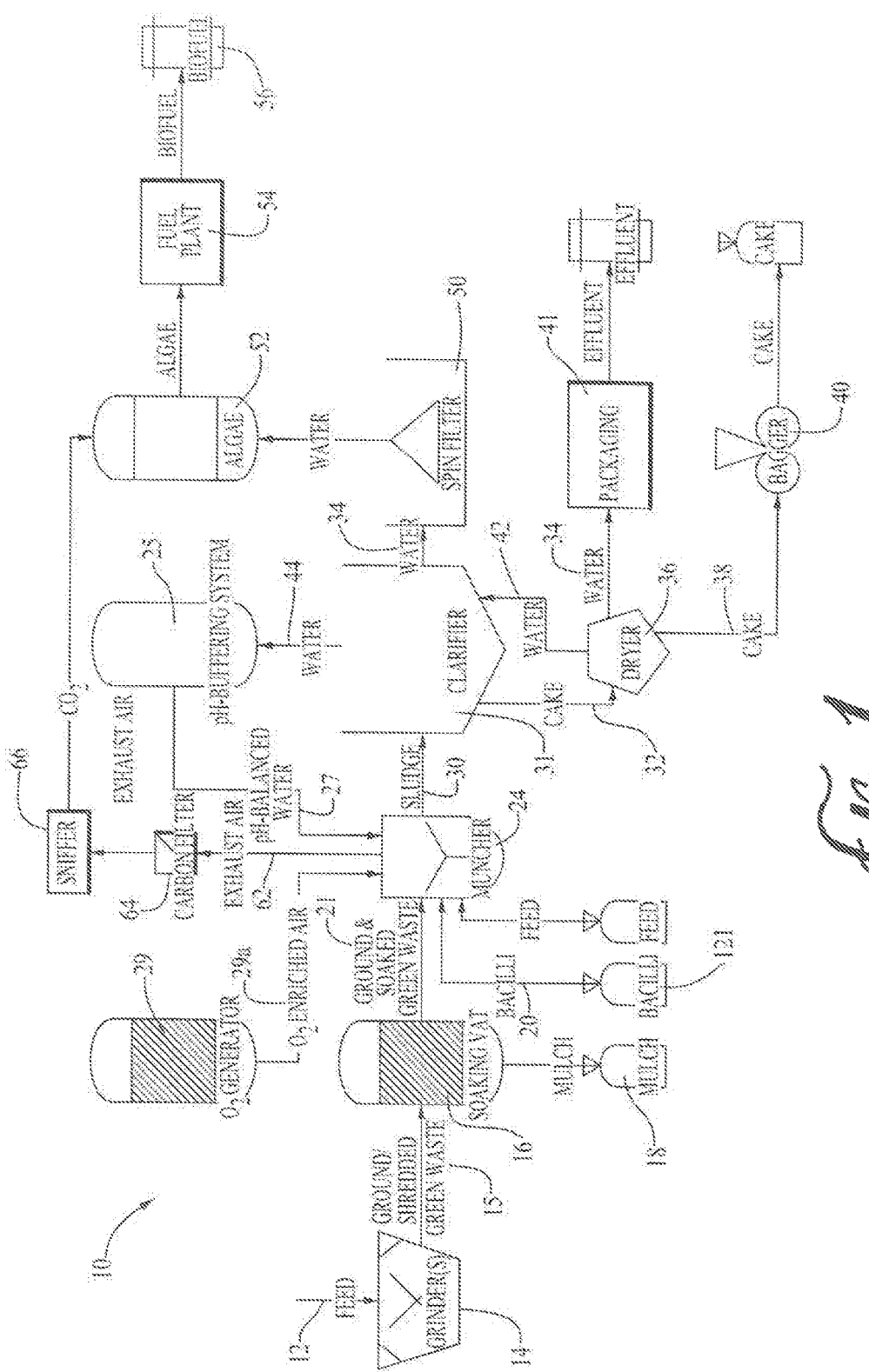
FIG. 1 is a schematic view of a system having features of the present invention.

With reference to FIG. 1, a system 10 having features of the present invention utilizes a biodegradable feed 12. Any suitable biodegradable feed 12 can be used such as biomass from farming, wood chips, and garbage. Other feeds 12 that can be used include human, animal and aquatic wastes, dead human, animal, and aquatic carcasses, fuels, hydrocarbons, manures, sludge, green waste, municipal solid waste, and all organic and many inorganic compounds including 1, 2 and 3 ring compounds that need to be degraded and reduced in either mass or toxicity. It is desirable that the feed 12 contains substantially no materials that are not biodegradable such as metal, glass, certain rubbers, and certain plastics. It can be determined if a particular feed material is suitably biodegradable for the system 10 by running tests on the material under the conditions of a digestion zone used in the system 10, as described herein.

The system 10 can be operated either as a batch process, continuous process, or semi batch.

If the feed 12 is not of sufficiently small size for easy biodigestion, the feed 12 can be comminuted in a comminution zone such as one or more grinders 14, that reduces the particle size to about ⅛ inch in diameter, or less. Preferably the feed is mechanically broken up to facilitate digestion by microorganisms by increasing surface area. While this is ensured by the grinder 14, other components can be used to mechanically reduce feed particle size throughout the process.

Comminuted material 15 from the comminution zone is transferred into an optional soaking zone that can be a vat 16. The transfer can be by gravity feed with the grinder 14 discharging downwardly into the soaking vat 16. The soaking vat 16 serves as a storage vessel to accommodate changes in feed rate of the feed 12, accumulating input material as it becomes available and discharging it as appropriate to maintain high system performance. In addition, it wets the feed for initiating digestion with any bacteria that may be present in the feed. Preferably the soaking zone is maintained at a temperature higher than ambient for accelerating digestion and killing pathogens. Preferably the average residence time in the soaking zone is at least 15 minutes, but can be less at elevated temperatures. Typically sufficient water is introduced into the soaking zone so that the water content of the soaking zone is at least 20%, and usually about 50%, by volume.

Optionally, some of the solids can be removed from soaking vat 16 as mulch 18. Soaked, inoculated and partially digested material from the soaking zone is introduced to an agitated digestion zone such as digestion vessel 24, also referred to as a muncher, such as by a pump or gravity feed. A preferred configuration for the digestion vessel 24 is described below.

Bacteria 20 is introduced into the digestion zone from storage 121. Preferred bacteria is that described in U.S. Pat. Nos. 6,025,152 and 6,562,585, which are incorporated herein by reference. This bacteria is preferred because it can digest biodegradable feed under aerobic, anoxic, and anaerobic conditions, allowing the system 10 to produce a variety of products, over a wide range of pHs, from about 2.5 to about 11.5. Preferably the pH is about 5 to about 11.5. Typically the bacteria is introduced in an amount to optimize the digestion process wherein essentially all of the biodigestible feed is digested, at the fastest digestion rate possible to maximize the amount of the material that is processed through the system 10. The digestion can be initiated with bacteria in the amount of about ⅕ gram per gallon of soaking zone where the initiation concentration is about $5 \times 10^9$ organisms per gram. A preferred bacteria composition is mixture A as described in the aforementioned U.S. Pat. No. 6,025,152. Individual organisms may be utilized or a combination of two or more or all organisms listed in aforementioned patent may be employed for a greater synergistic effect. The bacterial composition, Mixture A, comprises bacteria from the following families: *Bacillus subtillis*, *Bacillus sphaericus*, *Bacillus megatarium*, *Bacillus licheniformis*, *Enterobacter sakazakii*, *Bacillus coagulans*, *Bacillus cereus*, *Bacillus pasteurii*, *Bacillus cirroflagellosus* and *Bacillus pumilus*. The bacterial composition of Mixture A is present in the present invention from about 45 weight percent to about 100% total composition and preferably, from about 50 weight percent to about 90 weight percent, and most preferably from about 60 weight percent to about 70 weight percent of the total composition. The solid spores from the bacterial family of *Bacillus subtillis* (ATCC#465, 14617,14618) are present in the composition of the present invention from about 1 weight percent to about 20 weight percent, preferably about 6 weight percent to about 15 weight percent and most preferably about 10 weight percent of the total bacterial composition comprising Mixture A. The solid spores from the bacterial family of *Bacillus sphaericus* (ATCC#4525,10208,12123,12300) are present in the composition of the present invention from about 1 part to about 20 weight percent, preferably about 6 weight percent to about 15 weight percent and most preferably about 10 weight percent of the total bacterial composition comprising Mixture A. The solid spores from the bacterial family of *Bacillus megatarium* (ATCC#6458,6459,8245,10778) are present in the composition of the present invention from about 1 weight percent to about 20 weight percent, preferably about 6 weight percent to about 15 weight percent and most preferably about 10 weight percent of the total bacterial composition comprising Mixture A. The solid spores from the bacterial family of *Bacillus licheniformis* (ATCC#6634,8480,21416) are present in the composition of the present invention from about 1 part to about 20 weight percent, preferably about 6 weight percent to about 15 weight percent and most preferably about 10 weight percent of the total bacterial composition comprising Mixture A. The solid spores from the bacterial family of *Enterobacter sakazakii* (ATCC#12868,29004) are present in the composition of the present invention from about 1 part to about 20 weight percent, preferably about 6 weight percent to about 15 weight percent and most preferably about 10 weight percent of the total bacterial composition comprising Mixture A. The solid spores from the bacterial family of *Bacillus coagulans* (ATCC#7050,15949,35670) are present in the composition of the present invention from about 1 part to about 20 weight percent, preferably about 6 weight percent to about 15 weight percent and most preferably about 10 weight percent of the total bacterial composition comprising Mixture A. The solid spores from the bacterial family of *Bacillus cereus* (ATCC#6464,9139,10702,12480) are present in the composition of the present invention from about 1 part to about 20 weight percent, preferably about 6 weight percent to about 15 weight percent and most preferably about 10 weight percent of the total bacterial composition comprising Mixture A. The solid spores from the bacterial family of *Bacillus pasteurii* (ATCC#6452645311859) are present in the composition of the present invention from about 1 part to about 20 weight percent, preferably about 6 weight percent to about 15 weight percent and most preferably about 10 weight percent of the total bacterial composition comprising Mixture A. The solid spores from the bacterial family of *Bacillus cirroflagellosus* (ATCC#1441 1) are present in the composition of the present invention from about 1 part to about 20 weight percent, preferably about 6 weight percent to about 15 weight percent and most preferably about 10 weight percent of the total bacterial composition comprising Mixture A. The solid spores from the bacterial family of *Bacillus pumilus* (ATCC#7061,14884) are present in the composition of the present invention from about 1 part to about 20 weight percent, preferably about 6 weight percent to about 15 weight percent and most preferably about 10 weight percent of the total bacterial composition comprising Mixture A.

Optionally bacteria 20 can be introduced into the soaking zone 16, which optionally can be aerated or non aerated depending upon the desired environmental process.

Preferably the temperature in the digestion zone is at least 140° F., the recommended minimum temperature by the Environmental Protection Agency for killing pathogens. The digestion zone can be heated, not only to kill pathogens, but also to accelerate the action of the beneficial microorganisms. To accomplish this, the system can include heaters incorporated in the digestion zone, for example electrical heating elements attached to the outside of the inner vessel wall. Heaters can also be attached to the soaking vat 16 and other parts of the system. Optionally, tube heaters can be placed inside the digesting vat with hot liquid circulating through the tubes. Excess heat from the motors can be captured and utilized for this process, or generated by a flash heater fueled by gas generated by the anoxic or anaerobic process. Solar heating may also be employed.

A pH buffering system 25 buffers the pH within the system 10. It can do this by active means (e.g. chemical dosing, dictated by a control system in response to sensor inputs) or by passive means (e.g. passing circulating liquid through a bed of buffering material). It can be in line with fluid circulating between system components, or it can be configured in a loop with a single system component. The pH in the digestion zone can be controlled by adding a buffer 27 from the buffering system 25. Typical buffers are but not limited to CaO, MgO, MnO, NaOH, KOH, and pH rock. The digestion zone can be operated aerobically, by introducing an oxygen containing gas, such as air, oxygen, or air enriched with oxygen. Oxygen can be provided by an oxygen generating zone 29. The same line 29a used for introducing oxygen into the digestion vessel and can have a stub line (not shown) for introducing a gas such as but not limited to nitrogen or carbon dioxide.

The stub line and the line 29a for the oxygen generator 29, or nitrogen generator, or nitrogen gas generated from either the aerobic, anoxic or aerobic process, can be provided with conventional shut off valves (not shown) for switching from anaerobic or anoxic to aerobic operating conditions in the digestion zone. The system 10 can be operated anaerobically by not introducing any oxygen, since any oxygen present is consumed by the bacteria.

The change over from anaerobic, anoxic to aerobic or vice versa can occur in less than about 45 minutes, and preferably takes place in about 5 to about 30 minutes, merely by changing the gas flow into the digestion zone. The establishment of a nitrogen cycle, carbon cycle and other cycles with these bacteria takes place between one and forty-five minutes in either soil, water vapor, or aquatic environments. They can break down any biodegradable material between 1 to 45 minutes.

Thus an advantage of the system 10 using the preferred bacteria is it is possible to quickly change over from aerobic to anaerobic and vice versa. For example to switch from aerobic to anaerobic, the digestion zone can be flooded with a non-oxygen containing gas such as nitrogen. If the system 10 is operating anaerobically, it can be switched over to an aerobic process by introducing an oxygen containing gas.

The pressure in the digestion zone is typically atmospheric, but can go higher, up to about 10 atmospheres.

Higher pressure can increase the digestion rate, but equipment costs more when operating at elevated pressure.

Optionally an accelerant can be introduced to the soaking zone 16 and/or the digestion zone. A preferred accelerant contains a nitrogen source such as ammonia, a phosphorus source such as a phosphate, a potassium source such as potash, and a carbon source such as sugar. One such accelerant would be a mixture of ammonium phosphate, potash, and sugar. The amount of each ingredient depends on what the feed source lacks, which is available under the mark Super-Duper from Hiatt Distributors, Limited (www.HDLT-D.com).

The vessels used in the system can be constructed with abrasive or textured interior surfaces for further comminution of the feed beyond that provided by the grinder 14. For example, an abrasive lining can be fabricated by attaching a perforated sheet of material to the inside of the vessel 24, or by attaching it to raised ribs separating it from the inside of the digestion vessel 24. An abrasive lining can be fabricated by molding, pressing, or otherwise shaping the inside of the digestion vessel 24. An abrasive lining can be fabricated by attaching molded, pressed, or otherwise shaped pieces of material to the inside of the digestion vessel 24, for example, metallic, ceramic composite or glass tiles molded and fired with a toothed or abrasive surface or any combination of these materials.

The digested feed, referred to herein as sludge 30, flows from the digestion zone into a separation zone 31, also referred to as a settler or clarifier. Transfer can be affected with an auger screw, having an auger channel, or appropriate pump, or by gravity feed. The settler 31 separates the sludge 30 into a predominantly solid phase 32 and a predominantly liquid phase 34. The auger channel need not be parallel to the ground, but can slant downwardly toward or connect vertically with an output opening of the digestion vessel 24, to assist in removal of processed material, especially in the event of power failure or when it becomes necessary to empty the digestion vessel 24 following a batch cycle or for any other reason. The entire digestion vessel 24 (and other, attached components as necessary) can be permanently tilted from the horizontal axis for the same purpose.

The solid phase 32 from the settler 31 is optionally dried in a drying zone 36 such as by heat, mechanical drying such as a press, gravity separation, or filtration separation. The final product is a cake 38, which can serve as an excellent fertilizer or trace elements, which makes any non legume plants act as legumes and increases crop and flower yields by thirty percent or more and can be bagged in a bagger 40. Preferably the moisture content of the cake 38 is about 5%.

The digestion vessel 24 and discharge auger channel (and other, attached components as necessary) can be constructed such that a supporting framework is hinged at the output opening end of the digestion vessel 24, and not attached at the other end, so that the whole assembly can be tilted using e.g. permanently attached hydraulic cylinders or an overhead crane. Alternately, the supporting framework can be constructed with no attachment to the floor or other structures, and instead constrained horizontally by raised projections, e.g. blocks or bollards, or by locking mechanisms, such as latches or dogs, so that it can be tilted by e.g. hydraulic cylinders or an overhead crane. This feature can be occasionally used in removing processed material, as in a power failure. It can be for regular use, for example for emptying a digestion vessel intended for batch use. Liquid output 34 from the drying zone 36 can be packaged and sold as a liquid fertilizer.

A liquid packaging system 41 can weigh or volumetrically measure and package liquid byproduct from bottles, buckets, or other small or bulk packages, for transport and use or sale. Optionally some of the liquid output 34 from the drying zone 36 can be sent via recycle line 42 to the separation zone 31.

Water output from the separation zone 31 has many applications in the system 10. For example it can be recycled via line 44 for use in the buffering system 25. The bulk of the output water 34 can be passed for further clarification or processing, such as in a spin filter zone 50, where the output water can be used, because it contains nutrients, for growing algae in an algae cultivation zone 52 for use in a fuel plant 54 which can convert the algae to biofuel, Omega 3, feed stock for humans, aquatic life and animals and medicines 56. The output water can also be used in hydroponics to raise aquatic life and plants. The water can be processed further to elevate it to either the EPA standard for aquatic use or the standard for drinking water for humans.

Water 44 enters the buffering system 25 where pH adjusting agents such as calcium are provided. Aqueous buffer passes from the buffering system 25 via line 27 to the digestion zone as required.

Exhaust gas 62 from the digestion zone optionally can be filtered by a carbon or other filter 64 and then passed to a sensing system 66 for detecting the composition of the exhaust gas 62, such as the oxygen content, nitrogen content, methane content, hydrogen sulfate content, sulphur dioxide content, and carbon content, for controlling the digestion process. The digestion process is controlled by changing the temperature in the digestion zone, adding bacteria, changing pH, and/or changing the composition of the gas introduced to the digestion zone. The amount of carbon dioxide generated is an indication of the efficiency of the digestion process.

The exhaust gas 62 under anaerobic conditions is a fuel gas, containing high concentrations of methane. Thus under anoxic or anaerobic conditions, the output of the system 10 is fuel gas, predominantly methane, hydrogen sulfate, sulphur dioxide, nitrogen, and microorganisms. Under aerobic conditions, the output is cake, effluent and microorganisms for fertilizer, or when dehydrated, as a fuel source. The methane can be separated using membranes or cryogenically, and used or sold as fuel. Any hydrogen sulfate in the fuel gas can be used as feedstock for other processes (e.g. sulfuric acid production), or sold. Any sulfur dioxide in the fuel gas can be used as feedstock for other processes, or liquefied and sold. Nitrogen in the fuel gas can be used as feedstock or other processes, liquefied and sold.

Carbon dioxide produced by the metabolism of aerobic, anoxic and anaerobic microorganisms and vented from the digestion vessel and other system components can be captured for sale, sequestration, or use as a feedstock in other processes. Carbon dioxide can support algae growth. As noted above, the algae can be harvested and processed for sale or in the production of e.g. biodiesel, omega-3, or animal, aquatic or human feed and medicines.

An advantage of the preferred bacteria is that it retains sulfur and utilizes sulfur in its respiration process. Some liquid metabolic waste is converted into sulfuric acid and is contained in the effluent. This sulfur-laden water enhances the acceptance of the other compounds for plant or algae growth, such as phosphate, potash, or any other type of growth-enhancing compound. As a result, the effluent gas contains substantially none, if any, sulfur compounds such as hydrogen sulfide, sulfuric dioxide, and sulfuric acid.

When the digester is operating aerobically, the sulfur compounds are eliminated in the liquid metabolic waste of the bacteria as discussed in the previous paragraph. The primary gases generated are carbon dioxide, nitrogen, and water vapor.

When the digester is operating anoxically or anaerobically, the sulfur is absorbed into the liquid effluent in the form of either sulfite or sulfate compounds, such as, but not limited to, calcium sulfate or ammonium sulfate. The primary gases generated are carbon dioxide, water vapor, methane, hydrogen sulfide, nitrogen, and sulfur dioxide.

Figure 2:
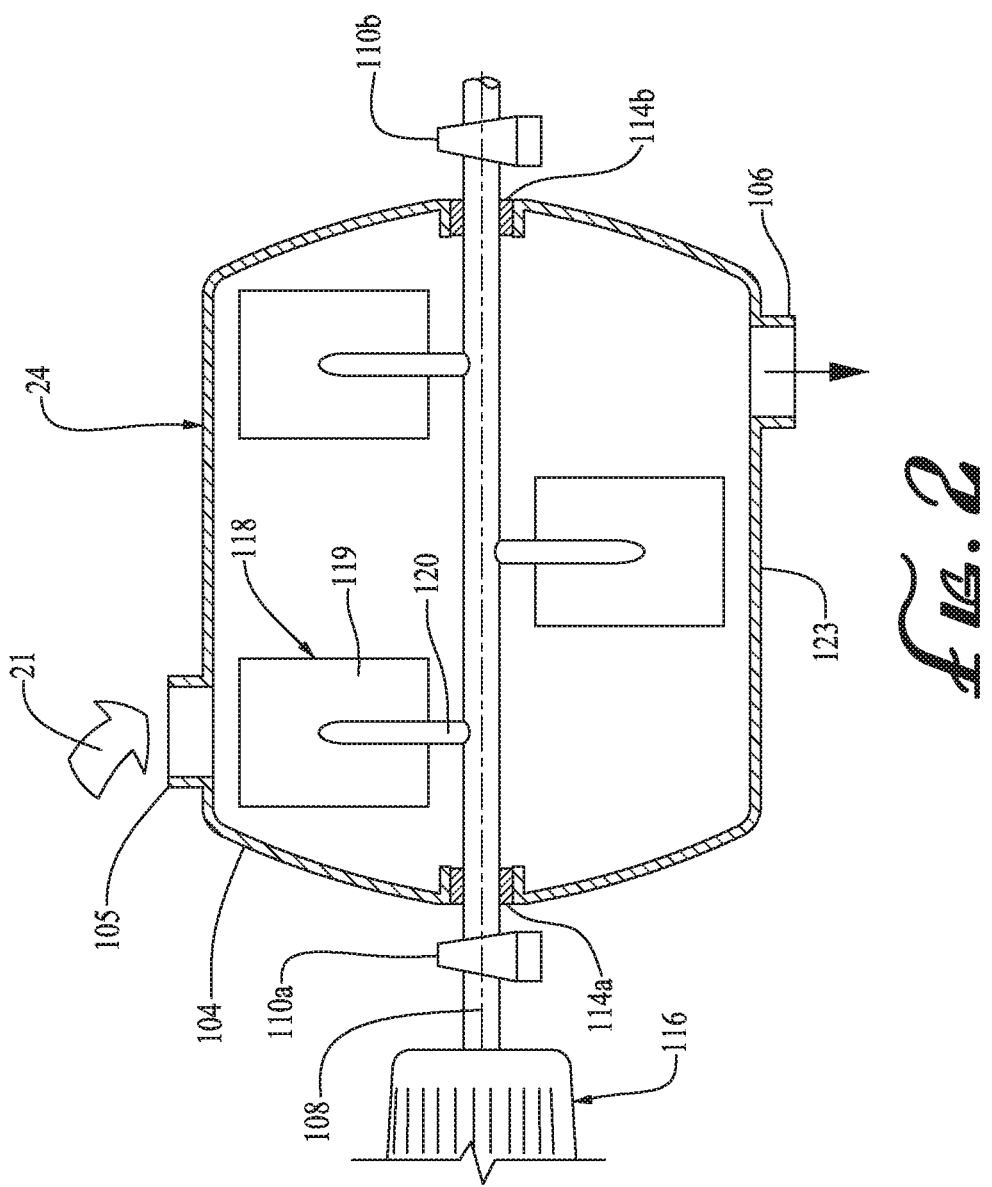
FIG. 2 is a cross-sectional view of a digester suitable for use in the system of FIG. 1.

With reference to FIG. 2, there is shown the preferred digestion vessel 24 for use as the digestion zone. The vessel 24 is generally cylindrical in shape with its longitudinal axis parallel to the ground. The digestion vessel 24 comprises an outer wall 104 and has an inlet 105 for the output 21 from the soaking zone 16 to be decomposed and acted on by microorganisms, and an outlet 106 for discharge of decomposed detoxified material. The inlet 105 and outlet 106 are preferably at opposite ends of the vessel 24 to maximize residence time in the vessel 24. The inlet 105 is at or near the top of the vessel 24 so that material can be added to the vessel using gravity, pump, or screw feed with no loss of previously added material. The outlet 106 is generally near the bottom of the vessel 24 so that processed material can be removed using gravity, pump, or screw feed flow. Material output from the digestion vessel 24 can be driven passively by gravity, for example by adjusting a valve at the vessel's output 106. Material can be removed by active mechanical means, for example an auger placed in a channel or bilge below the vessel volume swept by paddle rotation, and open to that volume, and rotating to move processed material longitudinally to e.g. a pipe or valve assembly.

It is desirable that the material in the vessel 24 be agitated. Any known agitation means to agitate contents of a vessel, including introduction of gas, ribbon type agitators, paddles, and the like can be used. Preferably paddles are used, with a rotating shaft 108 passing length wise through the vessel 24. The shaft 108 is supported in its substantially horizontal position by bearings 110a and 110b. The shaft 108 passes through seals 114a and 114b which prevent leakage of the contents of the vessel 24. The shaft 108 is driven by a motor 116. The paddle drive shaft 108 can be oriented vertically (in a "milkshake mixer" or "paint stirrer" configuration), as opposed to the horizontal orientation of FIG. 2. The paddle drive shaft 108 can in fact be oriented at any angle with respect to the horizontal.

A plurality of paddles 118, each having a blade 119 and a supporting rod 120, is secured to the shaft 108 to agitate the contents of the vessel 24. Each paddle 118 typically is attached to the shaft 108 by its supporting rod 120, which has a longitudinal axis substantially perpendicular to the longitudinal axis of the shaft 108. Preferably each paddle 118 is skewed relative to its supporting rod 120, wherein from a top view, some are skewed clockwise and others are skewed counterclockwise to obtain adequate agitation.

The digestion vessel 24 need not be cylindrical, but is a solid of revolution, with an internal diameter at any given point somewhat greater than the diameter swept by the corresponding paddles. The vessel can be much larger than the volume swept by paddles. The digestion vessel can be constructed in sections, so that in the event of a leak in one section, that section (housing) can be removed and replaced without replacing the entire vessel. The digestion vessel can also be constructed to be expandable to enable the processing of a larger volume of material. The digestion vessel can be constructed from metal, ceramic, plastics, or composites.

The paddles 118 can be permanently fixed to the shaft 108, for example welded, cast as a unit, or attached with an adhesive. The paddles 108 can be detachable, for example threaded onto the shaft or attached to collars mounted on the shaft by means of bolts or other threaded fasteners.

The shaft 108 need not have a circular cross-section. For example, it can have a hexagonal or square cross section inside the vessel, changing to a circular cross section where it passes through the seals 114 and bearings 110. The system can be operated such that material is not allowed to reach the level of the shaft 108, in which case the seals 114 are not necessary.

If the shaft 108 does not have a circular cross-section, collars can be fixed with respect to the shaft 108 by fitting the shaft's cross-section. If the shaft has a circular cross-section, collars can be fixed using keys, a shear pin press fitting, shrink fitting, adhesive, welding, or other methods. This pin or key can be made of a softer or weaker material, such that it will shear off when the paddle encounters excessive torque, preventing or reducing damage.

Regardless of shaft cross section, a collar can be assembled of two concentric pieces, similarly joined by a shear pin or key, for the same purpose.

One or more paddles can be attached to the shaft or to a collar at any point along the shaft. For example, a single collar can support one paddle; two paddles, 180 degrees opposed, or asymmetrically arranged; three paddles, 120 degrees opposed, or asymmetrically arranged; and so on.

There can be fewer paddle location points than the three shown in FIG. 2, or more. The vessel can include no paddles or shaft.

Paddles can be single pieces, or composed of arms and blades. In the latter case, the blade can extend down the arm all the way to the shaft or collar, past the end of the arm, or any subset.

The paddle blades 119 can be flat, curved about one or more axes, or formed in irregular shapes. They can be bent, for example in a dihedral angle. They can be solid, or they can have holes through them.

The blade 119 and rods 120 can be made of the same material, or of different materials. The blades 119 and rods 120 can be fabricated monolithically of the same material (e.g. by casting, forging, or machining from solid stock) or built up (e.g. by welding, gluing, or by using rivets or threaded fasteners).

The paddles 118 preferably span the length of the reaction vessel as straight segments or helical segments (as in the paddlewheel of a steamboat, or the blades of a reel lawn mower, respectively).

The paddles 118 can counter-rotate, driven by different shafts (i.e. entering the vessel from opposite ends, or concentric).

The paddles 118 can move material longitudinally with respect to the drive shafts, i.e. like propellers. This can enforce material movement inside a very long reaction vessel, or assist in aeration and input material breakdown within a smaller vessel.

The paddles 118 can be complemented by projections fixed to the interior wall of the reaction vessel 24. In the case of a rotating reaction vessel, these fixed projections can replace paddles fixed to a central shaft.

Material can also be agitated by other agitation means composed of multiple attached parts, moving or rotating with respect to one another: for example, chains, or chains with paddles attached to them.

Rather than a stationary reaction vessel 24 with rotating paddles inside, the system can employ a rotating reaction vessel with either fixed or counter-rotating paddles. This may require complex fittings for continuous use, but not for batch use. Batch use might be accomplished with something like a cement mixer.

The system can employ a rapidly rotating reaction vessel divided into concentric chambers by screens, filters, or other porous media, to centrifugally separate processed material into liquid and solid components (the "spin dry" configuration).

The vessel 24, as well as any other component of the system 10, can be made of any corrosion-resistance material, such as but not limited to stainless steel. Alternatively, the vessel 24 can be coated with a corrosion-resistant material. The material used for the vessel 24, as well as for the soaking vat 16, needs to be non-toxic to the microorganisms. Useful materials and combination of material include, but are not limited to, titanium, stainless steel, structural plastics, composite material such as carbon fiber and epoxy composites, ceramic, glass, and ceramic plates, supported by stainless steel, plastic or composite materials. Materials desirable include ceramics, Kevlar$_{TM}$-fiberglass combination, and a Teflon$_{TM}$ coating.

Preferably the digestion vessel 24 has a mesh screen 123 at least over the outlet 106, and preferably over the surface of the bottom half of the vessel or the sides of the vessel 24. The purpose of the screen 123 is to be certain the material in the vessel 24 is adequately digested before discharge. Typically the screen has a mesh size of about 1 to about 25 mm, and more preferably between about 3 and about 10 mm.

Due to the difficulty of supporting the long central shaft 108 partial-length shafts supported at both ends inside the vessel, and driven by e.g. a shaft entering the vessel perpendicularly, with gears, can be used; or propellers or other rotating ends on shafts entering the reaction vessel at an angle (like the propeller shaft passing through the hull of a boat or ship).

The digestion zone contents can be aerated by forcing air through stationary or moving nozzles or lances anywhere within the material volume. Vigorous oxygenation in this manner can also supplement or substitute for the action of paddles in mixing reaction vessel contents. This can also be accomplished by forcing air from the bottom or the sides, or by blowing it straight down. In paddle configurations, air can be forced through channels inside paddles (the "Hero's engine" configuration).

Forced ambient air can be enriched or entirely displaced by other gases (e.g. oxygen, nitrogen) or mixed gases, as appropriate, to improve system performance during aerobic, anaerobic, or anoxic operation.

Heat can be introduced to the digestion zone by preheating forced air used to oxygenate and agitate reaction vessel contents.

A heating system can incorporate heat exchangers for collecting waste heat from various components, e.g. the paddle drive motor, and heat friction from the moving parts. The heating system can include heat exchangers for absorbing heat from outputs (e.g. gaseous, liquid, and solid output) and returning it to the system. The heating system can include heat exchangers for pre-heating input air.

A single system can incorporate multiple reaction vessels 24 operating in parallel. For example, economical transportation might constrain an individual reaction vessel to a size inadequate for processing a site's material throughput. In this case, the system can be tailored to site requirements by employing multiple reaction vessels.

Multiple reaction vessels operating in parallel can also be used to increase a system's robustness and reduce overall system downtime. In a system employing multiple reaction vessels operating in parallel, an individual reaction vessel can be removed from service without halting operations altogether.

A single system can incorporate multiple reaction vessels operating in series. For example, processing particular types of material, or meeting local standards, might require series operation in order to guarantee a given residence time in this part of processing.

Multiple digestion vessels 24 operating in parallel and provided with bypasses can also be used to increase a system's robustness and reduce overall system downtime. In a system employing multiple digestion vessels operating in series, with bypasses, an individual reaction vessel can be removed from service without halting operations altogether.

Removing the end caps of the vessel allows the vessel to be expanded to whatever capacity the available space allows. The main body and ends can be split into sections which allows only certain parts of the vessel to be repaired. Such splitting can also enable the components to be easily stacked together for easier transportation and assembly.

An advantage of the present invention is that biomass can be brackish or have a high density when used with the preferred bacteria. The feed 12 can have a salt content wherein the liquid portion has a density of up to about 1.12. Thus the system can be used with feeds having a liquid portion with a density of about 1.009 to about 1.012. in a brackish liquid environment or higher saline densities up to 1.120. The biomass can also function in densities as low as 1.000.

Additional optional features of the system according to the present invention are discussed as follows:

Optionally, the digestion vessel 24 for the digestion zone can include an additional opening for introduction of microorganisms, in solid, granular form, or in aqueous solution. Microorganisms can be added to ensure that the population within the vessel and other parts of the overall system is adequate. Addition of microorganism is done when starting the system, and during routine operation. Microorganisms can be added manually, or by a microorganism dosing subsystem.

A microorganism dosing subsystem can be autonomous, responding to inputs from its own dedicated sensors, independent of other components and subsystems; or it can be controlled by a central automated control system. The microorganism dosing subsystem can add microorganisms more or less continuously; at scheduled intervals; or on an ad hoc basis, as determined by operator procedures, by sensor inputs, or by an automated control system processing sensor inputs. The microorganism dosing system can also add microorganisms using a combination of these approaches. For example, an automated control system can override a regular maintenance microorganism dosing schedule and accelerate microorganism dosing in response to inputs indicating a reduced microorganism population.

Microorganisms can also be added at other locations in the system, manually or automatically, on a regular schedule or in response to current conditions, etc.

Optionally, the vessel can include more than one inlet opening for introducing any organic or inorganic biodigestible feed in solid, paste, granular form, or in aqueous solution. Feed can be added using the opening for microorganism dosing. Feed can be added to ensure rapid growth of the population of microorganisms, or to maintain the population in the absence of adequate input material. This can be done when starting the system, and during routine operation. Feed can be added manually, by a dedicated feed dosing subsystem, or by the microorganism dosing subsystem described above. The feed dosing subsystem can be autonomous, responding to inputs from its own dedicated sensors, independent of other components and subsystems; or it can be controlled by a central automated control system.

The feed dosing subsystem can add feed more or less continuously; at scheduled intervals; or on an ad hoc basis, as determined by operator procedures, by sensor inputs, or by an automated control system processing sensor inputs. The feed dosing system can also add feed using a combination of these approaches. For example, an automated control system can override a regular maintenance feed dosing schedule and accelerate feed dosing in response to inputs indicating a reduced microorganism population.

Feed can also be added at other locations in the system, manually or automatically, on a regular schedule or in response to current conditions, etc.

Preferably the feed is mechanically broken up to facilitate digestion by microorganisms, by increasing surface area. While this is ensured by the grinder 14, other components can continue to mechanically reduce feed particle size throughout the process. The vessel can be constructed with abrasive or textured interior surfaces for this purpose.

For example, an abrasive lining can be fabricated by attaching a perforated sheet of material to the inside of the vessel 24, or by attaching it to raised ribs separating it from the inside of the digestion vessel. An abrasive lining can be fabricated by molding, pressing, or otherwise shaping the inside of the digestion vessel 24. An abrasive lining can be fabricated by attaching molded, pressed, or otherwise shaped pieces of material to the inside of the digestion vessel: for example, but not limited to metallic, ceramic or glass tiles molded and fired with a toothed or abrasive surface.

The system 10 can include a flash water heater for preheating water introduced to the system during start-up, solar heat or a standard water heater.

The digestion vessel 24 and other components (e.g. the soaking vat, clarifier, pipelines) can be insulated in order to maintain temperatures favorable to the microorganisms used, while minimizing energy consumption.

The digestion vessel 24 and other system components can be surrounded by jackets or systems of tubing through which heated air, water, or other fluids are forced, in order to maintain favorable internal temperatures.

Various system components can be driven by independent motors, or by a single motor and a system of gears, chains, belts, etc.

The system 10 can include a water filtration subsystem capable of producing potable water from clarified output 34. A water filtration subsystem output can be added to drinking water or irrigation systems, injected into aquifers or bottled. The water filtration system can incorporate a spin filter, a 3-4 step down filter, a carbon filter, an, ultraviolet radiation or ozone, a mixed bed filter and reverse osmosis.

The system 10 can be mobile, e.g. for use in demonstrations, on-site waste processing, and soil remediation, or optionally it can be sessile.

Other features of the system can include:
Feature A:
  A system for digesting biodigestible feed comprising:
  a) a digestion vessel;
  b) an inlet for introducing bacteria to the digestion vessel;
  c) agitation means such as paddle in the digestion vessel;
  d) an inlet for introducing an oxygen containing gas into the digestion vessel;
  e) an inlet for introducing biodigestible feed into the digestion vessel;
  f) an outlet for digested feed; and
  g) a control system for changing the contents of the digestion vessel from aerobic operation or to either anoxic or and, anaerobic operation in less than about 45 minutes, and as little as 1 minute without changing the bacteria in the digestion vessel.
Feature B:
  Feature A where the control system includes a valve for controlling introduction of oxygen containing gas into the digestion vessel.
Feature C:
  Feature A including a mesh screen limiting the particle size of material taken from the outlet.
Feature D
  The liquid phase of the contents of the vessel are either fresh, brackish, or high density salt contents having a density of greater than about 1 and up to about 1.12.
Feature E
  Feeds containing nitrogen, phosphate, potash, carbon and sulfur, the digestion vessel includes a gas outlet, and the gas contains substantially no sulfur containing compounds due to the choice of bacteria in aerobic environments.

What is claimed is:

1. A system for digesting biodigestible feed comprising:
   a) a digestion vessel containing contents;
   b) a gas inlet for introducing a gas into the digestion vessel; and
   c) a control system for changing (i) the composition of the gas introduced into the digestion vessel from the gas inlet, from an oxygen containing gas to a gas not containing oxygen for changing the contents of the digestion vessel from aerobic operation to either anoxic or anaerobic operation without changing bacteria in the digestion vessel for different bacteria and (ii) the composition of the gas introduced into the digestion vessel from the gas inlet from a gas not containing oxygen to a gas containing oxygen for changing the contents of the digestion vessel from anaerobic or anoxic operation to aerobic operation without changing bacteria in the digestion vessel for different bacteria.

2. A system for digesting biodigestible feed comprising:
   a) a digestion vessel containing contents;
   b) a gas inlet for introducing gas containing oxygen into the digestion vessel; and
   c) a control system for changing (i) the composition of the gas containing oxygen introduced from the gas inlet into the digestion vessel from oxygen containing to not containing oxygen which changes the contents of the digestion vessel from aerobic to either anoxic or anaerobic operation.

3. The system of claim 2 comprising an agitator for agitating the contents of the digestion vessel.

4. The system of claim 2 wherein the control system changes the contents of the digestion vessel from aerobic operation to either anoxic or anaerobic operation in less than about 45 minutes.

5. The system of claim 4 wherein the control system changes the contents of the digestion vessel from aerobic operation to either anoxic or anaerobic operation in about 5 to about 30 minutes.

6. The system of claim 2 comprising a valve for controlling introduction of oxygen containing gas into the digestion vessel through the gas inlet, the valve being controllable by the control system.

7. The system of claim 2 comprising a gas outlet from the digestion vessel.

8. The system of claim 7 comprising a filter for exhaust gas passing from the digestion vessel through the exhaust gas outlet.

9. The system of claim 2 comprising a soaking vat for soaking the feed prior to introduction of the feed into the digestion vessel through a feed inlet.

10. The system of claim 2 wherein the control system is adapted to maintain the contents of the digestion vessel at an elevated temperature of at least 140° F. for killing pathogens.

11. The system of claim 2 comprising a comminution zone for comminuting the feed prior to introduction into the digestion vessel through a feed inlet.

12. The system of claim 2 comprising a separator for separating digested feed from the digestion vessel into a predominantly solid phase and a predominantly liquid phase.

13. The system of claim 12 comprising a clarifier for the liquid phase from the separator.

* * * * *